United States Patent [19]

Mehra

[11] Patent Number: 5,018,522
[45] Date of Patent: May 28, 1991

[54] RAMPED WAVEFORM NON-INVASIVE PACEMAKER

[75] Inventor: Rahul Mehra, Stillwater, Minn.

[73] Assignee: Medtronic, Inc., Minneapolis, Minn.

[21] Appl. No.: 112,861

[22] Filed: Oct. 26, 1987

[51] Int. Cl.[5] .............................................. A61N 1/36
[52] U.S. Cl. ............................................. 128/419 PG
[58] Field of Search .................. 128/419 PG, 421, 422

[56] References Cited

U.S. PATENT DOCUMENTS

| | | | |
|---|---|---|---|
| 4,349,030 | 9/1982 | Belgard et al. | 128/419 PG |
| 4,372,319 | 2/1983 | Ichinomiya et al. | 128/421 |

OTHER PUBLICATIONS

Roy et al., "A More Efficient Waveform for Cardiac Stimulation", Med. & Biol. Engr. vol. 9 pp. 495–501 1971.
Bukstein, "Electric Shock on Purpose", Electronics World pp. 29–32, 97, 98; Feb. 1963.
Article Entitled "Pacemaker Clinic" by Victor Parsonnett, M.D., Published in *MCV Quarterly*, 7(4): 152–155, 1971.
Article Entitled "External Electric Stimulator for Treatment of Ventricular Standstill", by Leatham et al., Published in *The Lancet*, 2:1185–1189, 1956.
Article Entitled "External Electric Stimulation of the Heart", Published in the *Annals of the New York Academy of Sciences*, vol. III, pp. 932–937, Jun. 1964.
Brochure "Model 2018 External-Internal Pacemaker", Published by Medtronic, Inc. in 1969.
Brochure "Pace Aid 52" Distributed by Cardiac Resuscitator Corporation in 1985.

*Primary Examiner*—Edward M. Coven
*Assistant Examiner*—Jessica J. Harrison

[57] ABSTRACT

A non-invasive electrical stimulator for pacing the heart. The stimulator generates a ramped current waveform which reduces muscle stimulation and pain associated with external stimulation of the heart.

9 Claims, 6 Drawing Sheets

| 3a | 3c |
|----|----|
| 3b | 3d |

RAMPED WAVEFORM NON-INVASIVE PACEMAKER

BACKGROUND OF THE INVENTION

This invention relates generally to cardiac pacing and in particular to external, non-invasive cardiac pacing.

External non-invasive cardiac pacing is a well established technique which can provide effective heart pacing on an emergency basis. Traditionally, the pain and undesirable stimulation of skeletal muscles associated with non-invasive pacing have limited the acceptance of this technique.

Recent external pacemaker designs, such as that disclosed in U.S. Pat. No. 4,349,030 issued to Belgard et al, have addressed the problem of pain associated with external non-invasive pacing by providing constant current pacing pulses of extended duration. Typically, these pulses are 20 to 40ms in length and maintain a relatively constant current level throughout the duration of the pulse.

SUMMARY OF THE INVENTION

The present invention is directed to an improved external non-invasive cardiac pacemaker which can be tolerated by patients for an extended period of time. In particular, the present invention reduces the intensity of muscle stimulation associated with external non-invasive cardiac pacing by providing a ramped current pulse. In most patients, the use of a ramped current pulse as opposed to a constant current pulse significantly reduces skeletal muscle stimulation as compared to rectangular current pulses of the same amplitude and duration. In addition, use of a ramped waveform instead of a constant current waveform is believed to improve most patients' ability to tolerate extended periods of non-invasive pacing. Animal testing has revealed that the ramped current pulse is only slightly less efficient in stimulating the heart than the constant current pulse. The use of a ramped current waveform is believed to provide a non-invasive pacemaker which can generally be tolerated for longer periods of time than a constant current pulse generator.

The inventors have found that the response to external non-invasive pacing is highly individualized. Although generally muscle stimulation is reduced by extending the ramp time of the pacing pulse, the effect of such an extension varies from patient to patient. Further, the length of time a patient can tolerate external pacing is also related to the pain induced by the pacemaker. Pain also varies in a complex fashion with ramp time and differs from patient to patient. Therefore, the optimum ramp time varies from patient to patient. The present invention provides an adjustable ramp time to allow the pacing therapy to be optimized for each patient. The pacemaker allows adjustment of the ramp time and maximum pulse current amplitude to provide the most comfortable waveform consistent with reliably pacing the heart.

BRIEF DESCRIPTION OF THE DRAWINGS

FIG. 3, including

DETAILED DESCRIPTION OF THE DRAWINGS

Figure 1:
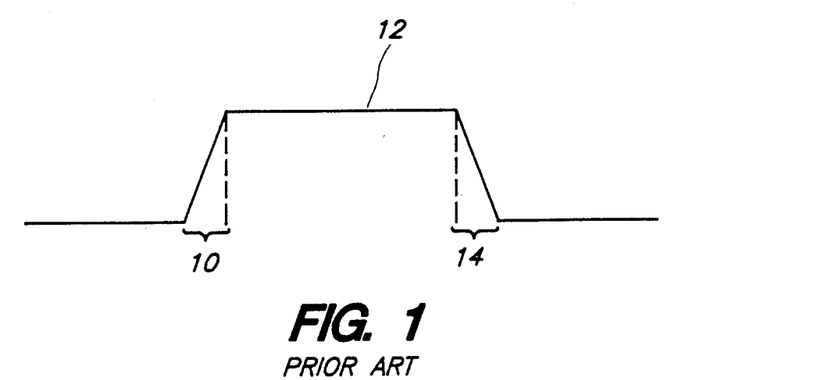
FIG. 1 illustrates a typical prior art constant current output waveform.

FIG. 1 shows a typical prior art constant current waveform of the sort used with present day external non-invasive cardiac pacemakers. Typically, the pulse is 20 to 40ms in duration. The rise time 10 and the fall time 14 of the pulse are typically on the order of 1 to 2ms. The pulse rapidly attains its predetermined maximum current level 12 rapidly and substantially maintains that current level throughout the duration of the pulse.

Figure 2:
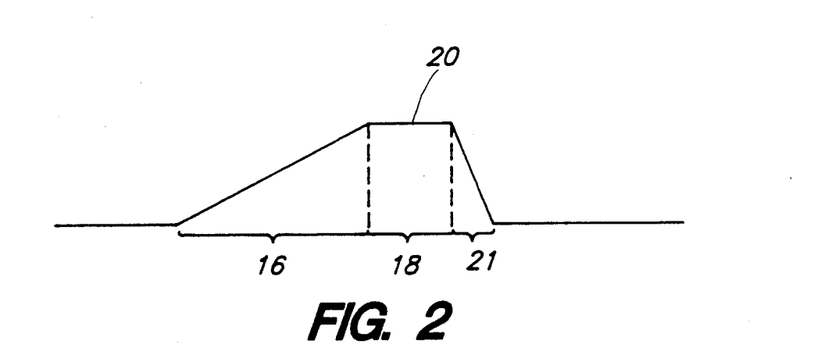
FIG. 2 illustrates a ramped current waveform according to the present invention.

FIG. 2 illustrates the output current pulse of a pacemaker according to the present invention. The overall duration of the pulse should be at least 20ms, and preferably at least about 40ms.

The current pulse of FIG. 2 differs from the prior art in that the pulse, instead of rising rapidly to its maximum current level 20, employs an extended, gradual rise. The rise time 16 of the ramped waveform if fixed should be a substantial portion of the duration of the waveform and, preferably, at least half of the duration of the waveform. The total duration of the waveform if fixed should be at least about 40ms. Generally, the maximum reduction in muscle stimulation occurs with a fully ramped waveform, e.g. 40ms duration and approximately a 40ms rise time. However, pacing efficiency starts decreasing more significantly with rise times in excess of 30ms. If rise time is also fixed, a rise time of between 20 and 40ms is believed advisable with 30–40ms preferable.

After reaching the maximum current level 20, the output pulse continues at this current level for a short period of time 18, and then rapidly returns to 0 over a short fall time 21 which may be 1 or 2ms. The time period 18 during which the pulse is at its maximum current level if fixed is preferably 0–10ms. Based on experimentation performed by the inventors, it appears that extending the fall time 21 of the ramped waveform generally provides no particular additional benefits, but may be desirable in some patients.

Figure 3:
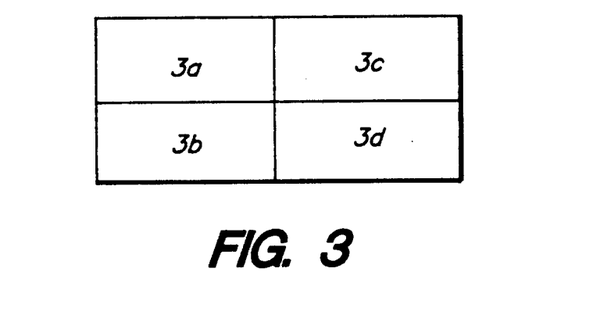

FIG. 3 illustrates the interconnection between the schematic diagrams of FIGS. 3a, 3b, 3c and 3d.

Figure 3A:
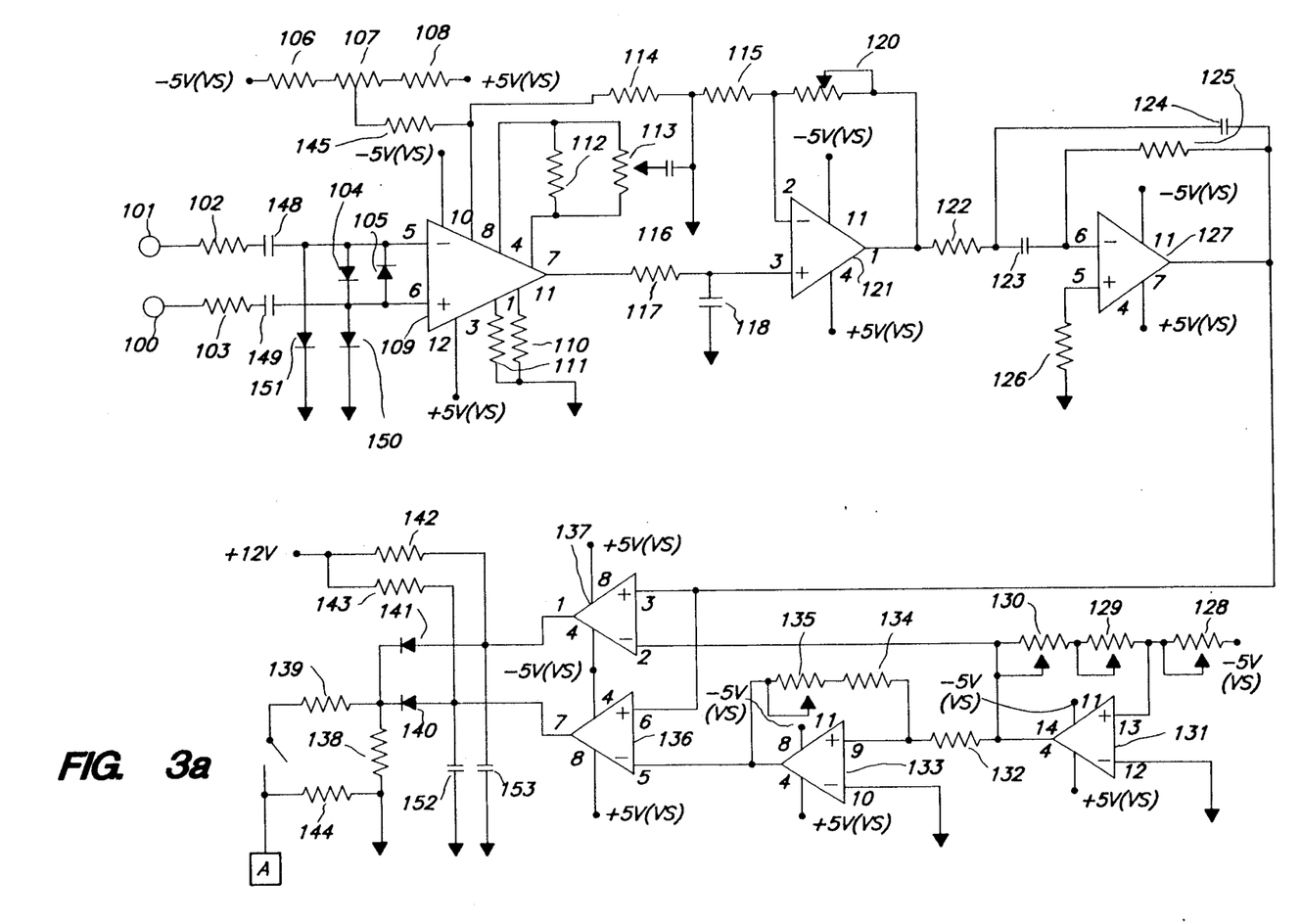
FIGS. 3a, 3b, 3c and 3d illustrates the schematic of a pacemaker according to the present invention which generates the pacing pulse of FIG. 2.

FIG. 3a illustrates the circuitry associated with the sensing of the patient's heartbeats. EKG electrodes 100 and 101 are coupled via resistors 102 and 103 and coupling capacitors 148 and 149 to the input of amplifier 109. Diodes 104 and 105 serve to protect amplifier 109 from the application of high voltages to electrodes 100 and 101. Diodes 150 and 151 limit the input voltages to amplifier 109 to one diode drop. Coupling capacitors 148 and 149 allow electrodes 100 and 101 to also be used to pace the heart. Amplifier 109, in conjunction with associated resistors 106, 107, 108, 110, 111, 112, 113, and 114, and capacitor 116, provides the initial amplification of the EKG signal. The DC offset of amplifier 109 is determined by resistors 106, 107, 108, 145 and 114, and adjusted by resistor 107. The common mode rejection capability of amplifier 109 is determined by resistors 112 and 113 in conjunction with capacitor 116. Adjustment is accomplished by resistor 113. Overall, amplifier 109 provides approximately a 2X gain.

The output of amplifier 109 is passed via resistor 117 and capacitor 118 to amplifier 121. Resistor 117 and capacitor 118 act as a low pass filter, allowing frequencies of approximately 70Hz and below to pass through to amplifier 121. Amplifier 121, in conjunction with associated resistors 115 and 120, functions as a noninverting amplifier, with a gain of approximately 50X. The output of amplifier 121 passes via resistor 122 and capacitor 123 to the input of amplifier 127. Amplifier 127, in conjunction with associated resistors 125 and 126 and capacitors 123 and 124, act as a band pass amplifier with a gain of approximately 4X to 8X. The band pass defined by the circuitry extends from approximately 0.5Hz to approximately 40Hz.

The output of amplifier 127 is passed through to amplifiers 136 and 137 which act as reference comparators, comparing the negative and positive amplitude of the output of amplifier 127 to positive and negative reference voltages. Amplifier 131, in conjunction with associated resistors 129 and 130, provides comparing amplifier 137 with a positive reference voltage adjustable from 0.5mv to approximately 10mv. R128 and R129 serve as internal high end and low end calibration resistors. Resistor 130 serves as the sensitivity control for the pacemaker. The output of amplifier 131 is also passed via resistor 132 to amplifier 133 which, in conjunction with associated resistors 134 and 135, sets the negative reference voltage provided to comparing amplifier 136. Adjustable resistor 135 provides an internal calibration adjustment to minimize the disparity between the positive and negative reference signals. If either the positive or negative going portion of the signal provided by amplifier 127 exceeds the reference value, an output signal is generated indicative of a sensed ventricular contraction and, in conjunction with resistors 138 and 139 and diodes 140 and 141, is passed through to reset the timing circuitry, discussed below. Resistors 142 and 143 serve as pull-up resistors. Capacitors 152 and 153 serve to provide a cleaner reset signal from the comparing amplifiers 136 and 137. Switch 146 is coupled to adjustable resistor 130, which serves as the sensitivity control. When switch 146 is open, no sensing of heart activity is accomplished, and the pacemaker operates in an asynchronous mode. Resistor 144 ties line 147 to ground in the event that asynchronous pacing is selected.

Figure 3B:
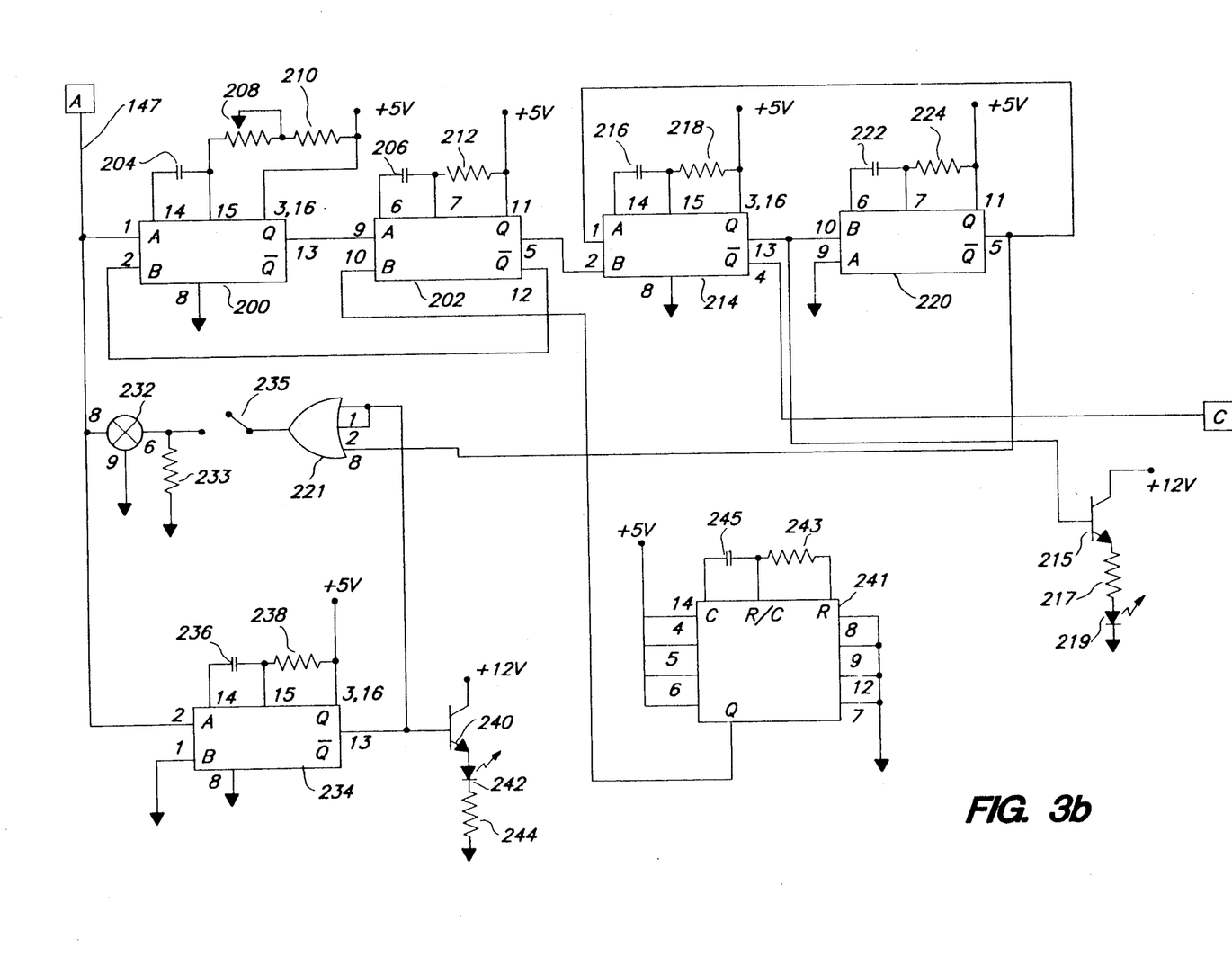

FIG. 3b shows the circuitry associated with the basic timing of pacing pulses. The retriggerable one-shots 200 and 202, along with their associated capacitors 204 and 206 and resistors 208, 210 and 212 serve to determine the basic pacing rate. Variable resistor 208 serves as the pacemaker's rate control The timing interval determined by one-shot 200 should be variable at least between about 1200ms and 500ms, but pacing intervals as short as 300ms may be desirable for some uses. The negative edge of the signal from comparator amplifiers 136 and 137 on line 147 reinitiates the timing period of one-shot 200, which determines the basic pulse interval and sets the Q output of one-shot 200 high. On the expiration of the timing interval determined by capacitor 204 and resistors 208 and 210, the Q output of one-shot 200 goes low. Oscillator 241, in conjunction with associated capacitor 245 and resistor 243, generates a 30KHz squarewave on line 160. When the Q output of one-shot 200 goes low, or on the positive going transition on line 160 thereafter, one-shot 202 is initiated. One-shot 202 then times out a 5ms interval determined by resistor 212 and capacitor 206, generating a 5ms low logic level pulse on its $\overline{Q}$ output which retriggers one-shot 200. As such, the pair of one-shots form a retriggerable, free running oscillator. The corresponding 5ms high pulse on the Q output of one-shot 202 triggers non-retriggerable one-shot 214 driving its Q output high.

One-shot 214, in conjunction with associated capacitor 216 and resistor 218, determines a 100ms interval during which the pacing pulse is generated. The low logic level pulse at the $\overline{Q}$ output of one-shot 214 serves to trigger the generation of a pacing pulse. The positive going transition of the high logic level output pulse from the Q output of one-shot 214 is used to trigger a second non-retriggerable one-shot 220, which serves as the rate limit for the pacemaker. The high logic level pulse on the Q output of one-shot 214 also activates transistor 215 to turn on LED 219 via resistor 217. LED 219 serves as a visual indicator of the generation of a pacing pulse.

One-shot 220, in conjunction with associated capacitor 222 and resistor 224 generates a 260ms high logic level pulse on the Q output of one-shot 220 which prevents further triggering of one-shot 214. This arrangement prevents any malfunction of the rate control one-shots 200 and 202 from causing the generation of pacing pulses in excess of about 230 beats per minute. Adjustment of the value of resistor 224 would allow for selection of the higher or lower rate limits.

The high logic level pulse on the Q output of one-shot 214 also serves to set the output of OR gate 221 high, which in turn couples line 147 to ground via digital switch 232. This prevents subsequent sensed contractions of the heart from restarting the timing period for at least the 260ms period determined by one-shot 214, thus providing a post-pacing blanking period.

Each time retriggerable one shot 200 is triggered by the sensing of a signal from comparator amplifiers 136 and 137 (FIG. 3a), non-retriggerable one-shot 234 is also triggered. One shot 234, in conjunction with capacitor 236 and resistor 238 generates a 100ms high logic level signal on its Q output. This turns on transistor 240, allowing current to flow through LED 242 and resistor 244. LED 242 indicates the sensing of a heartbeat. The visual indication of heartbeat sensing assists in adjustment of the sensitivity control, resistor 130 (FIG. 3a) to an appropriate level to reliably sense the heartbeat.

The Q output of one-shot 234 going high also sets the output of OR gate 221 high, tying line 147 low via digital switch 232 and associated resistor 233. Thus, one-shot 234 also provides a 100ms post-sensing blanking interval. Blanking functions can be disabled via switch 235.

Figure 3C:
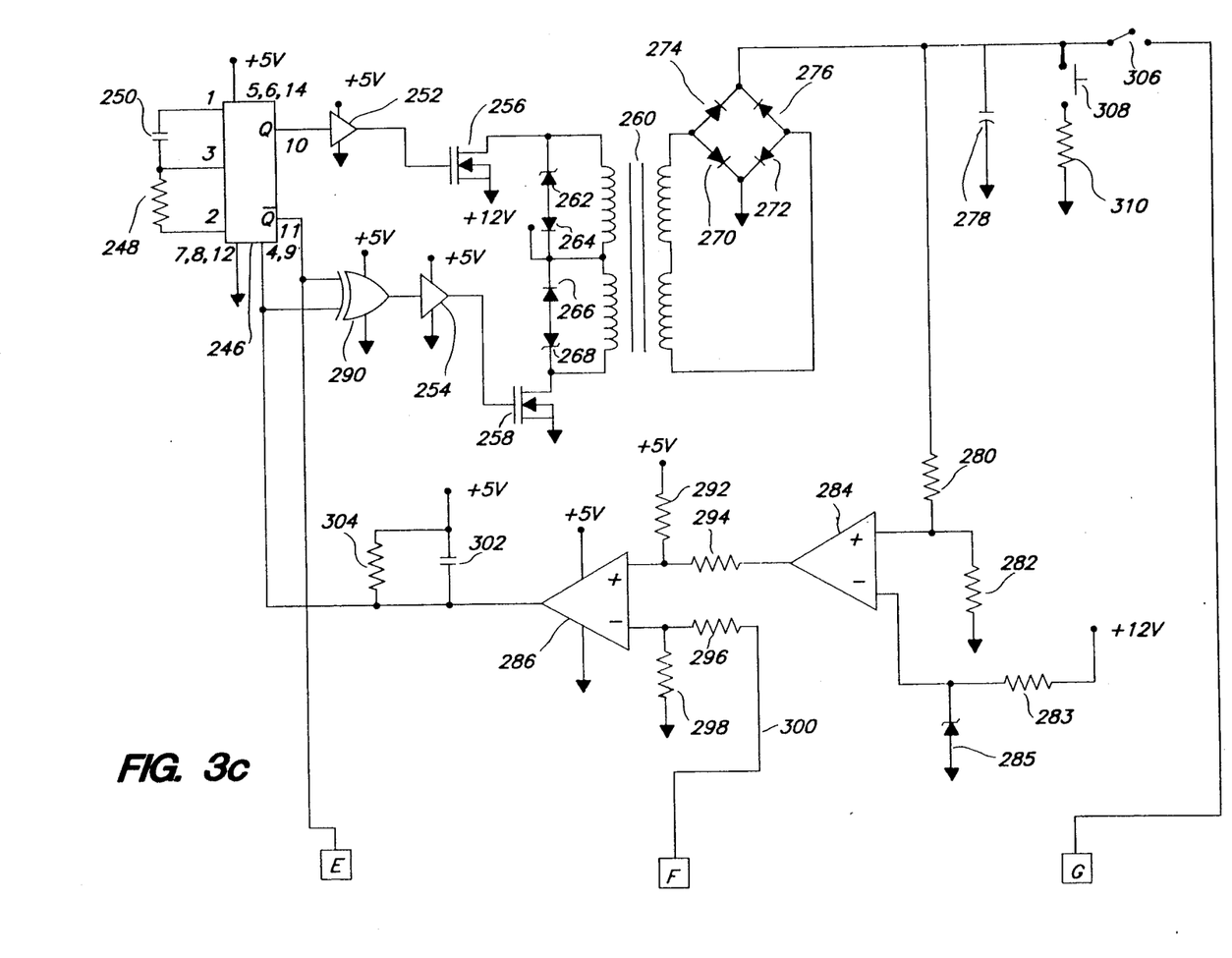

FIG. 3c illustrates the high voltage oscillator and the oscillator control circuitry. Multivibrator 246 in conjunction with timing resistor 248 and timing capacitor 250 is configured to provide 133KHz square wave signals on its Q and $\overline{Q}$ outputs, 90 degrees out of phase with one another. Amplifiers 252 and 254 are used as FET drivers to turn FET's 256 and 258, respectively, on and off in response to the signals generated on the Q and $\overline{Q}$ of oscillator 246. FET's 256 and 258 provide out of phase 12 volt, 133KHz signals to transformer 260. Transformer 260 steps up the $\pm 12$ volt signals to a $\pm 200$ volt signal, which is subsequently rectified by the diode bridge including diodes 270, 272, 274 and 276 and stored in capacitor 278.

The voltage stored in capacitor 278 is divided by a factor of 100 by resistors 280 and 282 which form a voltage divider. The divided voltage is compared by differential amplifier 284 to a 2 volt reference signal provided by resistor 283 and diode 285. When the voltage stored on capacitor 278 reaches 200 volts, oscillator 246 is turned off via differential amplifier 286, which generates a reset signal on line 288. The reset signal on line 288 sets the output of exclusive OR gate 290 low so that FET 258 will also be turned off when the oscillator is held on reset. This feature avoids unnecessary battery drain.

Differential amplifier 286, in conjunction with associated resistors 292, 294, 296 and 298 also serves as a comparator. Differential amplifier 286 is configured to also generate a reset signal for oscillator 246 in response to a high logic level signal on line 300, which is coupled to the output circuit and is high during generation of a pacing pulse. This prevents any signals from oscillator 246 from being superimposed on the pacing pulse. Capacitor 302 and resistor 304 serve to filter high frequency switching artifacts from the reset signal.

During generation of the pacing pulse, capacitor 278 is discharged, and passed through the output circuit. Switch 306 disconnects capacitor 278 from the output circuit. Switch 308 allows capacitor 278 to be discharged via resistor 310, and is provided to facilitate servicing the pacer.

Figure 3D:
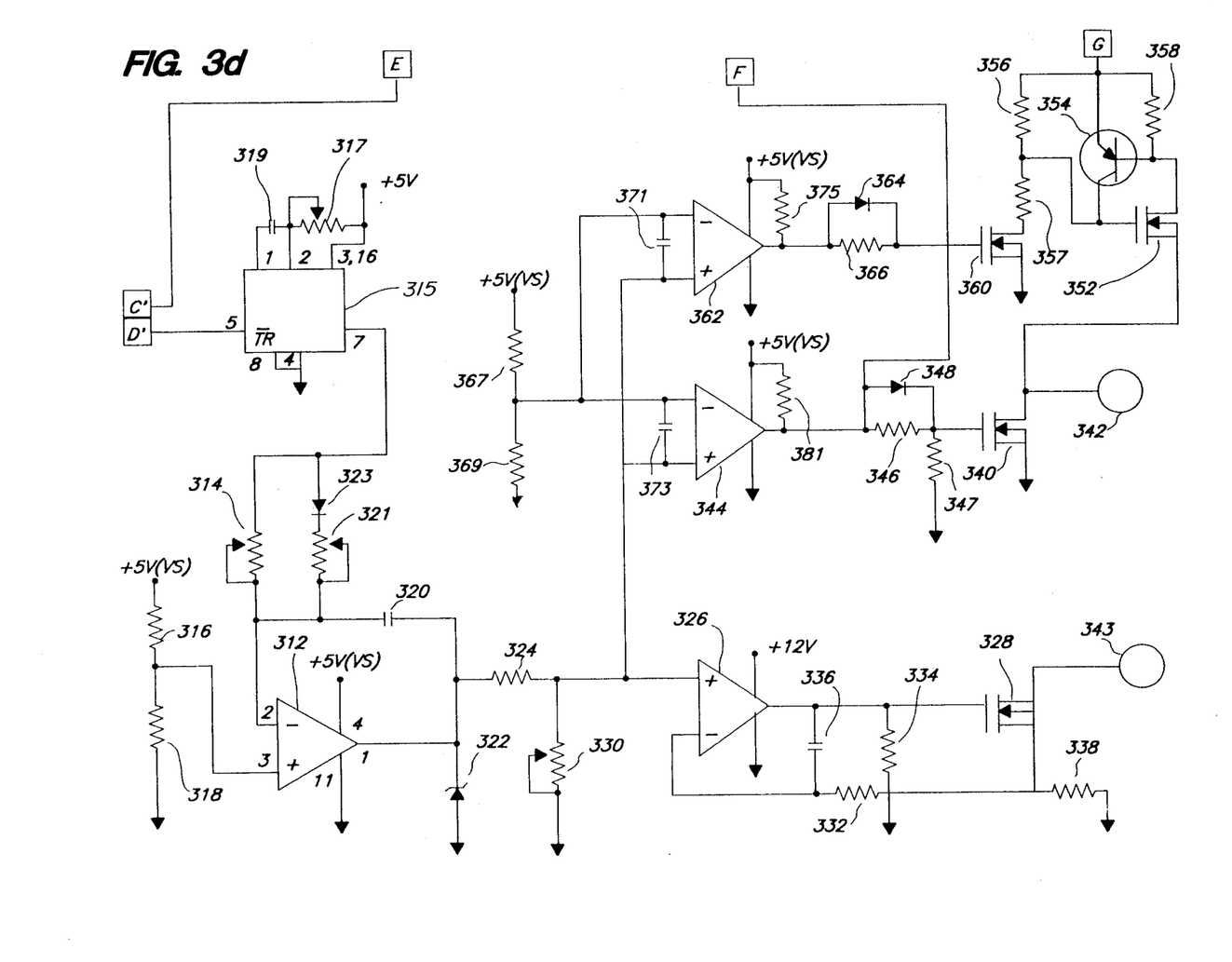

FIG. 3d illustrates the pulse generator of the pacemaker, including circuitry for generating the ramped output waveform. One-shot 315, in conjunction with associated resistor 317 and capacitor 319, determines the pulse width of the pacemaker. Resistor 317 serves as an adjustment for the pulse width, which may be adjustable between 0 and 40ms, or at least between 20 and 40ms.

Differential amplifier 312 and associated resistors 314, 316, 318 and capacitor 320 generate the ramp waveform. The 100ms square wave generated on the $\overline{Q}$ output of one-shot 214 (FIG. 3B) triggers one-shot 315.

The negative going logic pulse generated on the $\overline{Q}$ output of one-shot 315 is integrated by differential amplifier 312 and its associated circuitry, including resistors 316 and 318 and capacitor 320. Variable resistor 314 provides an adjustable rise time ramp. Variable resistor 321, in conjunction with diode 323, adjusts the fall time of the output pulse.

The ramped waveform provided by amplifier 312 is provided to amplifier 326 via resistor 324 and diode 322. Amplifier 326 is configured as a constant current amplifier. The output of amplifier 326 is used to control FET 328, which regulate's the current flow through the patient. As such, amplifier 326 in conjunction with FET 328 provides a ramped current waveform, having a ramp determined by the output of amplifier 312. Resistor 330 is used to regulate the output current, and resistors 332, 334 and capacitor 336 are used to filter out any transients generated by amplifier 326. Resistor 338 allows amplifier 326 to sample the current flowing through FET 328 and thus regulate the current.

FET 340 is used to ground patient electrode 342 between pacing pulses. FET 340 is turned off by amplifier 344 during pacing pulses. Resistor 346 and diode 348 ensure that FET 340 is turned on slowly following the pacing pulse to avoid clipping the pacing pulse. The output of comparing amplifier 344 is also provided to amplifier 286 (FIG. 3c) and is used to disable oscillator 246 (FIG. 3c) during the pacing pulse, as discussed above. Resistor 381 acts as a pull-up resistor. Capacitor 373 is used for common mode rejection.

FET 352 and associated transistor 354 and resistors 356 and 358 are used to connect the output of capacitor 278 (FIG. 3c) to patient electrode 342 during a pacing pulse. FET 352 is turned on by FET 360, which is controlled by amplifier 362. Comparing amplifier 362 turns on transistor 360 in response to the ramp output of amplifier 312 during the pacing pulse. Resistor 375 acts as a pull-up resistor. Capacitor 371 is used for common mode rejection. Diode 364 and resistor 366 ensure that FET 360 is turned off slowly. Transistor 354 is turned on whenever the current through FET 352 exceeds 200 milliamps, and serves to limit the current to 200 milliamps in case of component failure elsewhere in the circuit.

The output circuitry of FIG. 3d will require modification in those jurisdictions in which A-C coupled output stages are required by governmental regulation. Such modifications are believed to be well within the skill in the art.

Figure 4:
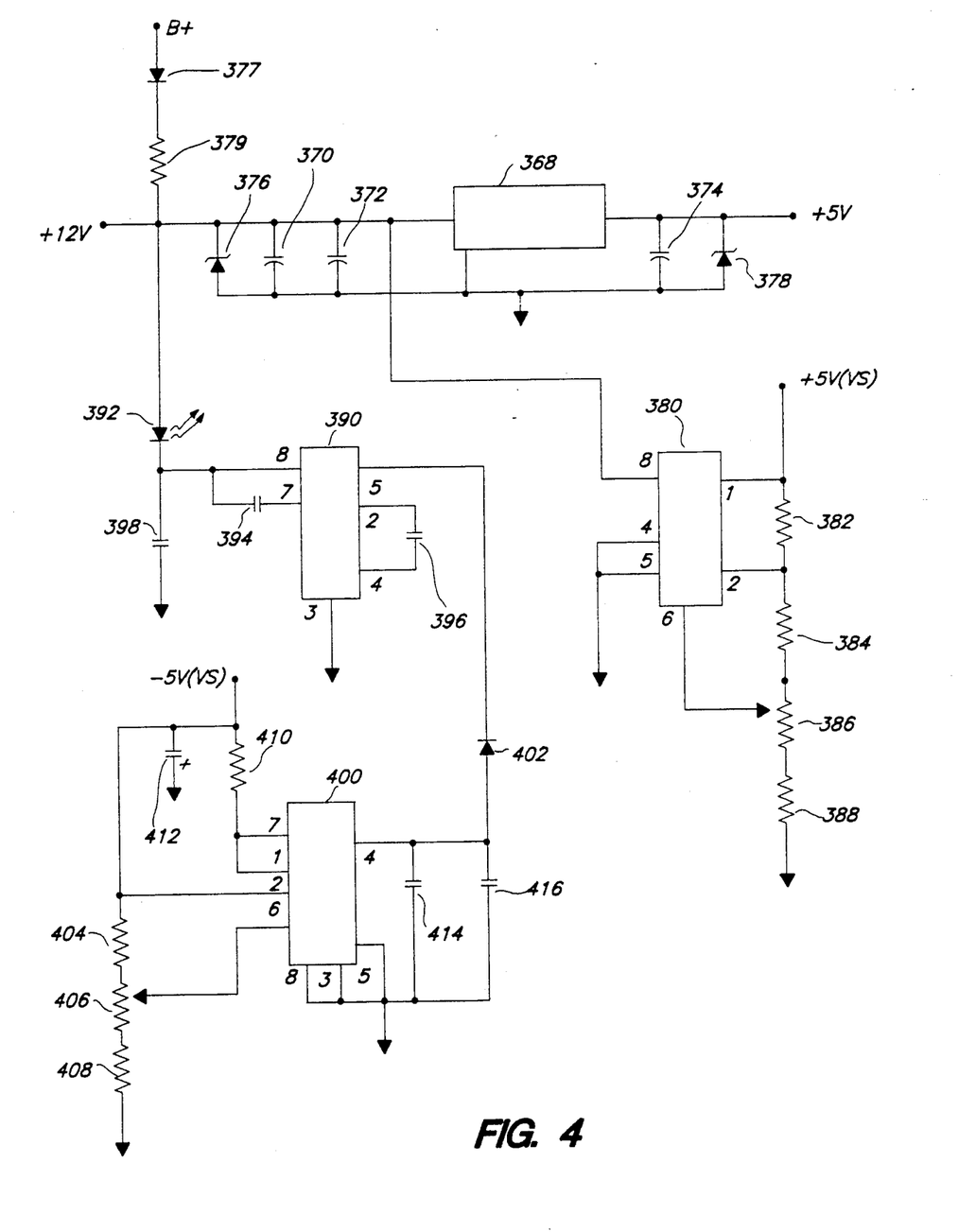
FIG. 4 is the schematic of the power supply for a pacemaker according to the present invention.

FIG. 4 illustrates the power and reference circuits used in the pacemaker. The battery provides a 12 volt power supply via diode 377 and resistor 379. Voltage regulator 368 and associated capacitors 370, 372, 374, and diodes 376 and 378 convert the 12 volt signal from the battery to the positive 5 volt signal used to drive the digital circuitry in the pacemaker. Capacitors 370, 372, 374 and diodes 376 and 378 provide filtering and voltage limiting.

Voltage regulator 380 and associated resistors 382, 384, 386 and 388 provide a positive 5 volt signal used by the linear circuitry in FIGS. 3a through 3d. Variable resistor 386 is used to calibrate the positive 5 volt signal.

The 12 volt signal provided by the battery is applied to voltage inverter 390 via LED 392, which acts as an indicator that the pacemaker is turned on. Voltage inverter 390, in conjunction with capacitors 394, 396 and 298, inverts the 12 volt signal from the battery and applies it to voltage regulator 400 via diode 402. Voltage regulator 400, in conjunction with resistors 404, 406, 408 and 410 and capacitors 412, 414 and 416, provides a negative 5 volt power signal to the linear circuitry illustrated in FIGS. 3a-3d. Variable resistor 406 is used for calibration of the positive 5 volt signal.

The design of the pacemaker allows the pacing pulse configuration to be adjusted to each patient. Generally, pain and muscle stimulation increase with increased pulse amplitude, but can often be reduced by extending the ramp time of the output pulse. Extending the duration of the output pulse generally allows use of lower pacing amplitudes. Generally, adjustment of the device should involve starting with a fully ramped waveform with a rise time of at least about 40ms and adjusting the amplitude control resistor 330 to the lowest maximum current level consistent with reliable capture of the heart, as indicated by an EKG monitor. The ramp time and amplitude may then be adjusted to determine whether a lesser ramp time may allow further reduction in the pulse amplitude required to reliably pace the heart. Adjustment of the amplitude and ramp times should continue until the patient indicates his maximum comfort level consistent with reliable pacing. After pacing for a period of time, the pacemaker may be readjusted if necessary. It is anticipated that some patients' ability to tolerate pacing for extended periods of time may be improved merely by regularly varying the pulse waveform.

COMPONENT LISTING

| Amplifiers | | Voltage Regulators | |
|---|---|---|---|
| 109 | LH0036C | 368 | LM2931A |
| 121,127,131,133 | LM224 | 380 | ICL7663 |
| 136,137,362,344 | LM393 | 390 | ICL7660 |
| 284 | TLC27L4 | 400 | ICL7664 |
| 326 | LM10C | | |
| 312,286 | TLC27M4 | Logic Gates | |
| | | 290 | CD4030 |
| Oscillators | | 252,256 | CD4050 |
| 241,246 | CD4047 | 221 | CD4075B |
| | | Diodes | |
| One-Shots | | 104,105,150,151 | 1N4007 |
| 200,202 | 74HC423 | 140,141 | 1N4148 |
| 214,220,234 | 74HC221 | 323,364,348,402 | 1N5711 |
| 315 | CD4098 | 322 | 1N750 |
| | | 376 | 1N5243 |
| Digital Switch | | 378 | 1N5235 |
| 232 | CD4066 | 270,272,274,377 | 1N4007 |
| | | 264,266,276 | 1N4007 |
| Transistors | | 262,268 | 1N974 |
| 240,215 | 2N2222 | 285 | LM113 |
| 354 | 2N2907 | | |
| 352 | MTP2P45 | LED's | |
| 360 | VN2406L | 392 | MLED600 |
| 340,328 | IRFF321 | 219 | LDH5191 |
| 256,258 | IRFD111 | 242 | LDY5391 |
| Resistors (Ω) | | Capacitors (F) | |
| 106,108,132 | 100K | 116 | .01u |
| 107,130,135 | 100K Adj. | 123,372,416 | .047u |
| 145 | 33K | 124 | .0047u |
| 102,103,366 | 20K | 204 | 15u |
| 112 | 52.3K | 206 | 1000p |
| 114 | 4.02K | 216,222,118,236 | .1u |
| 120 | 250K Adj. | 245 | 120p |
| 117 | 24.3K | 250,394 | 100p |
| 110,111,125 | 1M | 278 | 150u |
| 122 | 88.7K | 414,302,374 | 100u |
| 128 | 500K Adj. | 319 | 1.0u |
| 129 | 10K Adj. | 320 | .27u |
| 134 | 56K | 336 | 10pf |
| 142,143,139 | 100K | 370 | 2200u |
| 138 | 510K | 412,398,396 | 68u |
| 126,144,238 | 1M | 148,149 | .22u |
| 244 | 240 | 152,153,371,373 | .001u |
| 233,218 | 1M | | |
| 208,330 | 100K Adj. | | |
| 210 | 21K | | |
| 212,294,375,381 | 5K | | |
| 224 | 2.6M | | |
| 217 | 500 | | |
| 243 | 57.6K | | |
| 248 | 75K | | |
| 310 | 700 | | |
| 282 | 220K | | |
| 280 | 41.2M | | |
| 292,296,298 | 50K | | |
| 283,304,334 | 20K | | |
| 317 | 500K Adj. | | |
| 314,321 | 200K Adj. | | |
| 316,318,332 | 100K | | |
| 324 | 210K | | |
| 338 | 10 | | |
| 346 | 240K | | |
| 347,357 | 1M | | |
| 356 | 51K | | |
| 358 | 2 | | |
| 410,379,382 | 20 | | |
| 384,404 | 1.5M | | |
| 388,408 | 470K | | |
| 386,406 | 200K Adj. | | |
| 367 | 100K | | |
| 369 | 100 | | |

What is claimed is:

1. A non-invasive cardiac pacemaker, comprising:
first and second skin contacting electrode means for electrically coupling to a patient;
first timing means for repetitively timing an escape interval; and
pulse generator means, coupled to and responsive to said first timing means and coupled to said first and second skin contacting electrode means, said pulse generator means generating pacing pulses for application to said patient via said first and second electrode means, said pacing pulses extending for a duration of at least about 20ms, said pacing pulses having a current amplitude which rises gradually from 0 to a maximum current amplitude over a predetermined rise time of at least about 20ms.

2. A pacemaker according to claim 1 wherein said pulse generator means generates pacing pulses of at least about 40ms in duration, and in which the rise time of said pacing pulses extends for at least about 30ms.

3. A pacemaker according to claim 2 wherein the rise time of said pacing pulses extends for about 40ms.

4. A pacemaker according to claim 1 or claim 2 or claim 3 wherein the current amplitude of said pacing pulses pulse from said maximum current level to 0 in about 2ms or less at the expiration of said pacing pulse.

5. A pacemaker according to claim 1 wherein said pulse generator means further includes means for adjusting the rise time of said pacemaker pulses.

6. A pacemaker according to claim 5 wherein said pulse generator means generates pacing pulses having a duration of about 40ms and wherein said pulse generator means comprises means for adjusting said rise time of said pacemaker pulses at least between 30 and 4ms.

7. A pacemaker according to claim 1 wherein said predetermined rise time extends over substantially all of the duration of said pacing pulse.

8. A method of non-invasively pacing the human heart employing a pacemaker including pulse generator means for generating pacing pulses having a pulse duration, a maximum current amplitude, and a pulse rise time during which the amplitude of said pacing pulses rises from 0 to said predetermined maximum pulse current amplitude, and wherein said pulse generator means further includes means for adjusting the maximum current amplitude of said pacing pulses and means for adjusting the duration of said rise time of said pacing pulses up to a rise time substantially equal to the duration of said pacing pulses, comprising:
applying first and second skin contacting electrodes to the patient;
coupling said skin contacting electrodes to said pacemaker; and
adjusting said rise time of said pacing pulses and said amplitude of said pacing pulses while said patient indicates the level of discomfort associated with said pacing pulses, until said maximum pulse amplitude and said pulse rise time have been adjusted to provide the lowest available level of patient discomfort associated with reliable pacing of said patient's heart.

9. An external, non-invasive pacemaker comprising:
first and second skin contacting electrodes;
timing means for repetitively timing an escape interval; and
pulse generator means coupled to said timing means and responsive to the expiration of said escape interval for generating pacing pulses, said pulse generator means applying said pacing pulses to said first and second electrode means, said pulse generator generating pacing pulses having a duration of approximately 40ms and having a current amplitude rising gradually from 0 to a maximum current amplitude over a time period of at last 20ms.

* * * * *